United States Patent [19]

Mazour

[11] 4,079,103
[45] Mar. 14, 1978

[54] PROCESS FOR THE PRODUCTION OF PHOSPHITE CHLORIDES

[75] Inventor: Zdenek Mazour, Frenkendorf, Switzerland

[73] Assignee: Ciba-Geigy Corporation, Ardsley, N.Y.

[21] Appl. No.: 733,493

[22] Filed: Oct. 18, 1976

Related U.S. Application Data

[63] Continuation-in-part of Ser. No. 617,778, Sep. 29, 1975, abandoned.

[51] Int. Cl.$^2$ .............................................. C07F 9/20
[52] U.S. Cl. .................................... 260/972; 260/960

[58] Field of Search .............................. 260/960, 972

[56] References Cited

PUBLICATIONS

Cook, "J. Chem. Soci., " (London), (1949), IV, pp. 2921-2927.

*Primary Examiner*—Anton H. Sutto
*Attorney, Agent, or Firm*—Karl F. Jorda

[57] ABSTRACT

Process for the production of phosphite chlorides comprising the reaction of phosphorus trichloride and a trialkyl phosphite or a triphenyl phosphite in the presence of an aprotic solvent.

6 Claims, No Drawings

PROCESS FOR THE PRODUCTION OF PHOSPHITE CHLORIDES

This application is a continuation-in-part of Ser. No. 617,778, filed Sept. 29, 1975, now abandoned.

The present invention relates to a process for the production of phosphite chlorides of the formula I

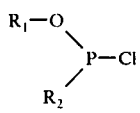

wherein
$R_1$ represents $C_1$-$C_{18}$-alkyl or optionally substituted phenyl, and
$R_2$ represents $OR_1$ or chlorine
by reaction of phosphorus trichloride with a symmetrical trialkyl- or triphenylphosphite that is present in the amount necessary for the formation of the phosphite chlorides or phosphite dichlorides.

Preferred among the compounds of the formula I are those in which $R_1$ represents $C_1$-$C_5$-alkyl. The radical $R_1$ as a phenyl group can be mono- to tri-substituted by $C_1$-$C_{18}$-alkyl, $C_1$-$C_{18}$-alkoxy or halogen, especially by chlorine or bromine, with the total number of carbon atoms for more than one alkyl or alkoxy group not being greater than 18.

The phosphite chlorides of the formula I obtainable by the process according to the invention, particularly those compounds in which $R_1$ represents an alkyl group having 1 to 5 carbon atoms and $R_2$ represents chlorine or an alkoxy group having 1 to 5 carbon atoms, are valuable intermediates for the production of O,S-dialkylthiophosphates of the type described in the U.S. patent applications Ser. Nos. 558,589, filed on Mar. 14, 1975, 377,855, filed on July 9, 1973, 394,694, filed on Sept. 6, 1973, 489,281, filed on July 17, 1974 and 408,874, filed on Oct. 23, 1973. By virtue of their excellent insecticidal action, these compounds can be used as pest-control agents.

The O,S-dialkylthiophosphates of the type described in the aforementioned patent applications are produced, for example, by reacting a dialkylchlorophosphite of the formula I with an alkylsulphenyl chloride to give the corresponding O,S-dialkylthiophosphoric acid chloride, which yields, by further reaction with a phenolate or enolate, the desired final product (see J. Org. Chem. 30, 3218, (1965)).

With the use of a variant of this process, the O,S-dialkylthiophosphates of the type described in the aforementioned applications can be produced by firstly reacting an alkylphosphite dichloride of the formula I with an alkylsulphenyl chloride to the corresponding S-alkylthiophosphoric acid dichloride, and replacing in this the two chlorine atoms successively by an alkoxy group and a phenoxy group.

The phosphite chlorides of the formula I can moreover be used as intermediates for the production of phosphites containing various alkyl groups or alkyl and phenyl groups in the molecule. Such mixed phosphites can be used for the stabilisation of epoxy compounds, and together with cadmium benzoate or cerium benzoate for the colour stabilisation or difficulty combustible polycarbonates (see U.S. Pat. No. 3,769,367 and British patent specification No. 1,180,836, which is based on the U.S. patent application Ser. No. 539,652, filed on Apr. 4, 1966).

A known process for the production of the dialkylphosphite chlorides and alkylphosphite dichlorides required as starting materials in the aforementioned processes for the production of O,S-dialkylthiophosphoric acid esters comprises reacting phosphorus trichloride in the presence of an acid acceptor, e.g. N,N-dimethylaniline or N,N-diethylaniline, with an alkanol (see H. G. Cook et al., J. Chem. Soc. 1949, Part IV, pp. 2921-2927, and A. J. Razumov et al., Chem. Abstr. 60, 1571g-h (1964). With this process the phosphite chlorides of the formula I are obtained merely in yields of 20 - 35% of theory. The processing of the reaction mixtures obtained is rendered difficult in that phosphine is formed as by-product, which constitutes a safety risk by virtue of its spontaneous inflammability. This process is therefore unsuitable for a production of phosphite chlorides on a commercial scale.

A variation of this process is described by J. Michalski et al., J. Chem. Soc. 1961, 4904, which comprises the use of a pyridine/diethylaniline mixture as an acid acceptor. Although higher yields can be obtained by this process, it is technically unsatisfactory on account of the necessary complicated working up of a mixture of hydrochlorides of two different bases.

It has also already been suggested that phosphite chlorides of the formula I be produced by reaction of trialkylphosphites with o-dihydroxybenzenephosphoric acid trichloride (see J. Gloede et al., J. Prakt. Chem. 316, 703-704, (1974)). Although it is possible by this process to obtain the phosphite chlorides of the formula I in a yield of 81% of theory, this process too is unsuitable for production of phosphite chlorides on a commercial scale since the o-dihydroxybenzenephosphoric acid trichloride required as starting material is on the one hand too expensive and on the other hand not available in large quantities. Furthermore, the process is rendered additionally costly as a result of the laborious processing of the cyclic o-dihydroxybenzenephosphate occurring in the reaction.

It is further known how to produce phosphite chlorides of the formula I by reaction of phosphorus trichloride with symmetrical trialkylphosphites (see J. Chem. Soc. 1949, IV, 2921-2927). There has thus been obtained for example, by refluxing for half an hour a mixture of triethylphosphite and phosphorus trichloride, diethylchlorophosphite in a yield of 44% of theory. In addition there were formed a small amount of higher-boiling products and a solid residue. In view of the low yield and the ecologically problematic by-products, this proccess too is unsuitable for the commercial production of alkylphosphite chlorides.

It has now been found that the phosphite chlorides of the formula I can be produced, in a short time and in yields appreciably higher than those hitherto obtained, by reaction of phosphorus trichloride with a symmetrical trialkylphosphite or triphenylphosphite that is present in the amount necessary for the formation of the phosphite chlorides or phosphite dichlorides if the said reaction of phosphorus trichloride with the symmetrical trialkyl phosphite or triphenylphosphite is performed in the presence of a polar aprotic solvent at a temperature of between $-15°$ and $+75°$ C. Suitable polar aprotic solvents are N-alkylated acid amides of carboxylic acids, of carbonic acid, of phosphoric acid or of alkyl- or arylphosphonic acids sulphoxides and sulphones. Particularly preferred aprotic solvents are hexamethylphosphoric acid triamide, N,N',N''-tris(tetramethylene)-phosphoric acid triamide (phosphoric acid tripyrrolidide), N,N'-bis-tetramethylene-n-butane phosphonic acid diamide, benzene phosphonic acid bis-dimethylamide, dimethylformamide, dimethylsulphoxide, tetramethylurea, morpholine-N-carboxylic acid-N',N'-dimethylamide and sulpholane, The amount of aprotic polar solvent that is added to the reaction mixture is preferably between 0,05 and 10 Mol.-%, preferably 1-3 Mol.-%, relative to the total molar number of the starting products. The reaction can however be performed also in the presence of appreciably greater amounts of aprotic solvents.

Within the temperature range of −15° to 75° C. in which the reaction can be carried out, the preferred range is that between −5° and 40° C, especially between 0° and 25° C.

The reaction is performed according to the invention by a process in which one of the two reactants is brought together with the aprotic solvent and the second reactant is then added.

The choice of aprotic polar solvent in the presence of which the reaction of symmetrical trialkyl- or triphenylphosphites and phosphorus trichloride is performed depends on the boiling point of the final products. There must always be a sufficiently large temperature difference between the boiling points of the final products on the one hand and the aprotic polar solvent on the other hand in order to avoid the possibility of the aprotic polar solvent getting into the distillate during separation (by distillation) of the phosphite chloride of the formula I, since otherwise there would occur in the distillate anew a rapid distortion of the equilibrium between symmetrical trialkyl- or triphenylphosphite and phosphorus trichloride on the one hand and the alkyl- or phenylphosphite chloride just produced, on the other hand. It is advantageous to perform the distillation-separation of the phosphite chloride of the formula I at as low a temperature as possible. Provided that they are not immediately further processed, the alkyl-phosphite chlorides or phenylphosphite chlorides of the formula I produced according to the invention can be stored with cooling for a prolonged period.

With a further simplification of the process of the invention the procedure can be such that phosphorus trichloride is reacted with a compound of the formula R₁OH in the presence of a stoichiometric amount of an amine base, such as triethylamine or pyridine, and an inert solvent, such as benzene, toluene or chlorobenzene, to give trialkyl- or triphenylphosphite, the appropriate amount of aprotic solvent is added and the phosphorus trichloride is added dropwise. After separation of the precipitated amine hydrochlorides, the further processing is then performed as described above.

By carrying out according to the invention the reaction of symmetrical trialkyl- or triphenylphosphite with phosphorus trichloride in the presence of an aprotic polar solvent the result achieved is that the equilibrium between trialkyl- or triphenylphosphite on the one hand and phosphorus trichloride on the other hand is established particularly rapidly and under mild conditions. It is thus possible, for example, to process by distillation the reaction mixture immediately after addition of the second constituent. By virtue of this considerable shortening of the reaction times and the avoidance of higher reaction temperatures, which are possible as a result of carrying out the process according to the invention, there is avoided the formation of undesired by-products, e.g. the formation of spontaneously inflammable phosphines such as readily occur with longer retention times at temperatures of above 60° C. At the same time, the yield of the desired final product compared with the yield obtained by known processes is greatly increased. The process of the invention thus renders possible for the first time the nonproblematic large-scale commercial production of phosphite chlorides of the formula I; moreover, this production can be carried out also in the form of a continuous process. Furthermore, the phosphite chlorides of the formula I can be produced in a particularly pure form by the process of the invention.

The process of the invention is further illustrated by the following Examples.

EXAMPLE 1

Dimethylchlorophosphite 32.5 g (0.24 mole) or phosphorus trichloride is slowly added dropwise to a mixture, cooled to 0° to 5° C, of 62.04 g (0.5 mole) of trimethylphosphite and 4.0 g of hexamethylphosphoric acid triamide. The reaction mixture is subsequently heated to about 20° C and stirred for a further 2 hours at this temperature. The formed dimethylchlorophosphite is isolated by distillation under reduced pressure from the reaction mixture. There is obtained 68.13 g (74.5% of theory relative to the phosphorus trichloride) of dimethylchlorophosphite, b.p. 29°–31° C/35 Torr.

EXAMPLE 2

Diethylchlorophosphite 130 g (0.95 mole) of phosphorus trichloride is added dropwise in the course of 1 hour, with stirring, to a mixture, cooled to 0° to −5° C, of 332 g (2.0 moles) of triethylphosphite and 15.65 g of hexamethylphosphoric acid triamide. The reaction mixture is subsequently heated to 20° to 25° C and stirred for a further 1 hour at this temperature. The formed diethylchlorophosphite is isolated by distillation under reduced pressure from the reaction mixture. There is obtained 330 g (74% of theory relative to the phosphorus trichloride) of diethylchlorophosphite, b.p. 40°–41° C/12 Torr.

The same result is obtained by commencing with a mixture, cooled to 0° to 5° C, of 130 g (0.95 mole) of phosphorus trichloride and 15.65 g of hexamethylphosphoric acid triamide, and adding dropwise to this mixture 332 g (2.0 moles) of triethylphosphite.

EXAMPLE 3

Di-n-butylchlorophosphite 32.5 g (0.24 mole) of phosphorus trichloride is added dropwise in the course of 30 minutes, with stirring, to a mixture, cooled to 0° to 5° C, of 125.2 g (0.5 mole) of tri-n-butylphosphite and 4.0 g of hexamethylphosphoric acid triamide. The reaction mixture is subsequently heated to 20° to 25° C and stirred for a further 2 hours at this temperature. On vacuum distillation of the reaction mixture there is obtained 106 g (70% of theory relative to the phosphorus trichloride) of di-n-butylchlorophosphite, b.p. 96° – 98° C/10 Torr.

EXAMPLE 4

Diphenylchlorophosphite 32.5 g (0.24 mole) of phosphorus trichloride is added dropwise, with stirring, to a mixture, cooled to 0° to 5° C, of 155.2 g (0.5 mole) of triphenylphosphite and 10.0 g of hexamethylphosphoric acid triamide. The reaction mixture is subsequently heated to room temperature and stirred at this temperature for a further 4 hours. On vacuum distillation of the reaction mixture there is obtained 110 g (61.1% of theory relative to phosphorus trichloride) of diphenylchlorophosphite, b.p. 170°–172° C/11 Torr.

EXAMPLE 5

Diethylchlorophosphite 65.0 g (0.48 mole) of phosphorus trichloride is added dropwise at 15° to 20° C in the course of 1 hour, with stirring, to a mixture of 166.0 g (1.0 mole) of triethylphosphite and 20.0 g of tetramethylurea, with the temperature being kept continuously below 30° C. After completion of the addition, the reaction mixture is stirred at 20° to 30° C for 80 hours and subsequently distilled under reduced pressure. There is obtained 145 g (65% of theory relative to phosphorus trichloride) of diethylchlorophosphite, b.p. 40°–41° C/12 Torr.

EXAMPLE 6

Ethyldichlorophosphite 137 g (1.0 mole) of phosphorus trichloride is added dropwise at 20° to 30° C, with stirring, to a mixture of 83 g (0.5 mole) of triethylphosphite and 10.0 g of hexamethylphosphoric acid triamide. The yellowish suspension obtained is heated to 50 C and stirred for a further 15 hours at this temperature. After removal by filtration of an insoluble residue, a filtrate is obtained which consists to the extent of about 92–95% of ethyldichlorophosphite. The yield is about 92–95% of theory. On vacuum distillation of the filtrate there is obtained 187–198 g (85–90% of theory relative to phosphorus trichloride) of ethyldichlorophosphite, b.p. 47°–52° C/13 Torr. For the further reaction, there can of course be used in most cases the crude ethyldichlorophosphite.

EXAMPLE 7

Didecylchlorophosphite 3.42 g (0.025 mole) of phosphorus trichloride is added dropwise at 25° to 30° C, with stirring, to a mixture of 25.14 g (0.05 mole) of tridecylphosphite and 1.5 g of hexamethylphosphorus acid triamide. After completion of the addition, the reaction mixture is stirred for a further 5 hours at 25° to 30° C. There is obtained 27.5 g of crude didecylchlorophosphite in the form of a non-distillable viscous oil (yield 96% of theory).

EXAMPLE 8

Diethylchlorophosphite 32,5 g (0,237 mole) of phorphorus trichloride is slowly added dropwise to a mixture, cooled to 0° to 5° C, of 83.0 g (0.5 mole) of triethylphosphite and 4.0 g of dimethylsulphoxide while the whole mixture is cooled and stirred vigorously. After addition of the phosphorus trichloride the cooling bath is removed and the reaction mixture is stirred for 24 hours at room temperature. Subsequently, the diethylchlorophosphite formed is isolated from the reaction mixture by distillation under reduced pressure whereby a Vigreux-Column (length 15 cm) is used. There is obtained 88.6 g (79% of theory relative to phosphorus trichloride) of diethylchlorophosphite, b.p. 40°–41° /12 Torr.

EXAMPLE 9

Diethylchlorophosphite 32.5 g (0,237 mole) of phosphorus trichloride is slowly added dropwise to a mixture, cooled to 0° to 5° C, of 83 g (0,5 mole) of triethylphosphite and 3,91 g of dimethylformamide while the whole mixture is cooled and stirred vigorously. After addition of the phosphorus trichloride the cooling bath is removed and the mixture is stirred for 24 hours at room temperature. Then the diethylchlorophosphite formed is isolated by distillation under reduced pressure whereby a Vigreux-Column (length 15 cm) is used. There is obtained 91,2 g (81.8% of theory relative to phosphorus trichloride) of diethylchlorophosphite, b.p. 40°–41° C/12 Torr.

EXAMPLE 10

Diethylchlorophosphite 68.5 g (0,5 mole) of phosphorus trichloride is slowly added dropwise, with stirring, at 25°–30° C to a mixture of 166,0 g (1 mole) of triethylphosphite and 4,0 g of phosphoric acid tripyrrolidide (N,N′,N″-tris-(tetramethylene)-phosphoric acid triamide). After addition of the phosphorus trichloride the reaction mixture is stirred for half an hour. Then the crude diethylchlorophosphite is separated from the phosphoric acid tripyrrolidide by quick distillation under reduced pressure. There is obtained 230 g of crude product, b.p. 13°–40° C/10 Torr, containing 205 g (87,2 g of theory relative to phosphorus trichloride) of diethylchlorophosphite. The residue remaining in the reaction vessel which essentially consists of phosphoric acid tripyrrolidide and small amounts of by-products can be used as catalyst for the next batch.

EXAMPLE 11

Diethylchlorophosphite 22,6 g (0,165 mole) of phosphorus trichloride is added dropwise at room temperature while stirring to a mixture of 54,8 g (0,35 mole) triethylphosphite and 1,22 g (0,0049 mole) of n-butane phosphonic acid dipyrrolidine. During addition of the phosphorus trichloride the temperature raises to 29° C. After addition of the phosphorus trichloride the reaction mixture is stirred for 6 hours at 30° C. The mixture thus obtained contains 84% of theory of diethylchlorophosphite which is separated from the n-butanephosphonic acid dipyrrolidide by distillation under reduced pressure. At a temperature of 40° to 41° C and a pressure of 12 to 13 Torr 70,4 g of distillate is obtained containing 62 g (80% of theory relative to phosphorustrichloride) of diethylchlorophosphite.

EXAMPLE 12

Diethylchlorophosphite 68,8 g (0,5 mole) of phosphorus trichloride is added dropwise at room temperature, while stirring, to a mixture of 166 g (1 mole) of triethylphosphite and 4,6 g of benzenephosphonic acid bis-dimethylamide. During addition of the phosphorus trichloride the temperature raises to 28° C. After addition of the phosphorustrichloride the reaction mixture is stirred for 24 hours at 30° C. Subsequently the diethylchlorophosphite is separated from the reaction mixture by distillation under reduced pressure. At a temperature of 40° to 42° C and a pressure of 13 Torr 173,8 g of distillate is obtained containing 156 g (66,5% of theory relative to phosphorus trichloride) of diethylchlorophosphite.

I claim:

1. A process for the production of phosphite chlorides of the formula

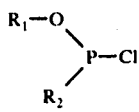

wherein
R$_1$ represents C$_1$-C$_{18}$ alkyl, phenyl or phenyl mono-, di or tri-substituted by C$_1$-C$_{18}$, alkyl, C$_1$-C$_{18}$ alkoxy or halogen with the total number of carbon atoms for more than one alkyl or alkoxy group not being greater than 18, and R$_2$ represents OR$_1$ or chlorine, wherein R$_1$ has the definition given above which comprises reacting phosphorus trichloride with a symmetrical trialkyl- or tri(substituted) phenyl phosphite that is present in the amount necessary for the formation of the phosphite chlorides of formula 1 in the presence of a polar aprotic solvent at a temperature of between −15° and +75° C.

2. Process according to claim 1 wherein the polar aprotic solvents used are N,N-dialkylated acid amides of carboxylic acids, of carbonic acid, of phosphoric acid or phosphonic acids, alkyl- or arylphosphoric acids, sulphoxides or sulphones.

3. Process according to claim 1 wherein there is used a polar aprotic solvent from the group hexamethylphosphoric acid triamide, N,N',N"-tris-(tetramethylene)-phosphoric acid triamide, N,N'-bis-tetramethylene-n-butane phosphonic acid diamide, benzene phosphonic acid bis-dimethylamide, dimethylformamide, dimethylsulphoxide, tetramethylurea and sulpholane.

4. Process according to claim 1 wherein the polar aprotic solvent is used in an amount of 0,05 to 10 Mol-%, relative to the total molar number of the starting products.

5. Process according to claim 1 wherein the reaction is performed in the temperature range of −5° to +40° C.

6. Process according to claim 1 wherein the reaction is performed in the temperature range of between 0° and 25° C.

* * * * *